US012780910B2

(12) United States Patent
Tavassi et al.

(10) Patent No.: US 12,780,910 B2
(45) Date of Patent: Nov. 3, 2026

(54) ANTI-INFLAMMATORY PEPTIDES, PHARMACEUTICAL COMPOSITION CONTAINING SUCH PEPTIDES AND USES THEREOF

(71) Applicant: INSTITUTO BUTANTAN, São Paulo (BR)

(72) Inventors: Ana Marisa Chudzinski Tavassi, São Paulo (BR); Miryam Paola Alvarez Flores, São Paulo (BR); Yara Cury, Santana de Parnaíba (BR); Michelle Cristiane Bufalo, Cerquilho (BR); Irina Kerkis, São Paulo (BR); Fernanda Menezes Cerqueira, São Paulo (BR); Eduardo Osorio Frare, São Paulo (BR)

(73) Assignee: Instituto Butantan, São Paulo (BR)

( * ) Notice: Subject to any disclaimer, the term of this patent is extended or adjusted under 35 U.S.C. 154(b) by 1215 days.

(21) Appl. No.: 17/641,378

(22) PCT Filed: Sep. 9, 2020

(86) PCT No.: PCT/BR2020/050360
§ 371 (c)(1),
(2) Date: Mar. 8, 2022

(87) PCT Pub. No.: WO2021/046626
PCT Pub. Date: Mar. 18, 2021

(65) Prior Publication Data

US 2022/0324958 A1 Oct. 13, 2022

(30) Foreign Application Priority Data

Sep. 9, 2019 (BR) ..................... 10 2019 01 8666 6

(51) Int. Cl.

| | |
|---|---|
| ***C07K 14/435*** | (2006.01) |
| ***A61K 35/646*** | (2015.01) |
| ***A61P 19/02*** | (2006.01) |
| ***A61P 29/00*** | (2006.01) |
| ***C07K 7/06*** | (2006.01) |
| ***C07K 14/81*** | (2006.01) |
| ***C07K 16/24*** | (2006.01) |

(52) U.S. Cl.
CPC ............ *C07K 16/24* (2013.01); *A61K 35/646* (2013.01); *A61P 19/02* (2018.01); *A61P 29/00* (2018.01); *C07K 7/06* (2013.01); *C07K 14/43527* (2013.01); *C07K 14/8114* (2013.01)

(58) Field of Classification Search
CPC ........ C07K 14/43527; C07K 14/43513; C07K 14/43563; C07K 14/8114; A61P 29/00; A61P 19/02
See application file for complete search history.

(56) References Cited

U.S. PATENT DOCUMENTS

| | | | |
|---|---|---|---|
| 2009/0042786 | A1 | 2/2009 | Maria et al. |
| 2009/0170182 | A1 | 7/2009 | Chudzinski-Tavassi et al. |
| 2016/0108086 | A1 | 4/2016 | Giudicissi-Filho |

FOREIGN PATENT DOCUMENTS

| | | | |
|---|---|---|---|
| WO | WO-2006029492 | A1 | 3/2006 |
| WO | WO-2009093189 | A2 | 7/2009 |
| WO | WO-2017197253 | A2 * | 11/2017 |
| WO | WO-2020102874 | A1 | 5/2020 |

OTHER PUBLICATIONS

Accegen product page for NHAC-kn (human articular chondrocytes). www.accegen.com/product/human-articular-chondrocytes-abc-tc3968/; downloaded Oct. 31, 2025 (3 total pages).*
Braz-De-Melo et al. Potential neuroprotective and antiinflammatory effects provided by omega-3 (DHA) against Zika virus infection in human SH-SY5Y cells. Sci Reports 9: 20119, 2019 (12 total pages).*
Buri et al. cAmbly: A non-toxic cell-penetrating peptide derived from Amblyomin-X with targeted delivery to mitochondrial and cytoplasmic proteins. PLoS One 20(3): e0318119, 2025.*
Cao et al. miR-296-5p inhibits IL-1β-induced apoptosis and cartilage degradation in human chondrocytes by directly targeting TGF-β1/CTGF/p38MAPK pathway. Cell Cycle 19(12): 1443-1453, 2020.*
English Translation of WO 2020102874; May 28, 2020.*
Kaya et al. Optimizing SH-SY5Y cell culture: exploring the beneficial effects of an alternative media supplement on cell proliferation and viability. Sci Reports 14: 4775, 2024 (11 total pages).*
Ko et al. Substance P, A Promising Therapeutic Target in Musculoskeletal Disorders. Int J Mol Sci 23: 2583, 2022 (14 total pages).*
Maia Lobba et al. C-terminal portion of Amblyomin-X interacts with Tom70 and acts as an immunomodulatory molecule in macrophages. FEBS Open Bio 12(Suppl S1): 40, ShT-03.3-4, 2022.*
Oliveira et al. Amblyomin-X peptide: targeting macrophages for inflammatory disease treatement. Osteoart Cartukage 33: 820, #839, 2025.*
Xicoy et al. The SH-SY5Y cell line in Parkinson's disease research: a systematic review. Mol Neurodegen 12: 10, 2017 (11 total pages).*

(Continued)

*Primary Examiner* — Bridget E Bunner

(57) ABSTRACT

Various sequences of new peptides and derivatives with anti-inflammatory effects in various cellular models (chondrocytes osteoclasts, macrophages derived from THP-1, and neurons) in the context of stimulus-induced inflammation widely known in the literature for each model. The compounds were shown to be able to reverse the expression of molecules associated with the cell's inflammatory mechanism, in addition to inducing regenerative proteins and reducing pain markers. Accordingly, the claimed compounds of the present invention can be applied to degenerative diseases of an inflammatory nature including rheumatoid arthritis and osteoarthritis.

5 Claims, 10 Drawing Sheets

Specification includes a Sequence Listing.

(56) References Cited

OTHER PUBLICATIONS

Zhao et al. Per2 attenuates LPS-induced chondrocyte injury through the PTEN/PI3K/Akt signalling pathway. Biosci Report 40: BSR20200417, May 28, 2020 (8 total pages).*

Dadar Maryam et al: "Antiinflammatory peptides: current knowledge and promising prospects", Inflammation Research, Birkhaeuser Vers Lag, Basel, CH, vol. 68, No. 2, Dec. 17, 2018 (Dec. 17, 2018), pp. 125-145, XP036677019, ISSN: 1023-3830, DOI: 10.1007/S00011-018-1208-X [retrieved on Dec. 17, 2018] the whole document.

Pazelli Gabriela Simões et al: "Effect of protein rLOPAP and peptide derived on human chondrocytes in the inflammatory model with interleucin-1 [beta]", Toxicon, Elmsford, NY, US, vol. 168, 0107, Jul. 10, 2019 (Jul. 10, 2019), p. S41, XP085805436, ISSN: 0041-0101, DOI: 10.1016/J. Toxicon.2019.06.162 [retrieved on Jul. 10, 2019] abstract.

M.P. Alvarez-Flores et al: "Development of a high content screening assay for the screening of proteins and peptides in a model of osteoarthritis", Osteoarthritis and Cartilage, vol. 27, Apr. 1, 2019 (Apr. 1, 2019), p. S200, XP055769699, GB ISSN: 1063-4584, DOI: 10.1016/j.joca.2019.02.309 abstract.

Ana Claudia Sato et al: "Exploring the in vivo wound healing effects of a recombinant hemolin from the caterpillar", Journal of Venomous Animals and Toxins Including Tropical Diseases, Biomed Central Ltd, Longon, UK, vol. 22, No. 1, Dec. 21, 2016 (Dec. 21, 2016), pp. 1-8, XPO21241405, DOI: 10.1186/S40409-016-0093-4 the whole document.

Akkiraju, H., Nohe, A. Role of Chondrocytes in Cartilage Formation, Progression of Osteoarthritis, and Cartilage Regeneration. Journal of developmental biology. 2015; 3: 177-192.

Alvarez-Flores, M. P., Fritzen, M., Reis, C. V., Chudzinski-Tavassi, A. M. Losac, a factor X activator from *Lonomia obliqua* bristle extract: its role in the pathophysiological mechanisms and cell survival. Biochem Biophys Res Commun. May 19, 2006;343(4): 1216-23.

Fritzen, M.; Schattner, M.; Ribeiro, A. L. Q.; Batista, I. F. C.; Ventura, J.; Prezoto, B. C. & Chudzinski-Tavassi, A. M. A prothrombin activator (Lopap) modulating inflammation, coagulation and cell survival mechanisms. Biochemical and biophysical research communications, v. 333, n. 2, p. 517-523, 2005.

Goldring, M. B.; Otero, M. Inflammation in osteoarthritis. Current opinion in rheumatology, v. 23, n. 5, p. 471, 2011.

He, X.; Huang, L.; Qiu, S.; Yin, X.; Shen, Y.; Wu, Y.; Jiang, Y.; Fang, J. β-Endorphin attenuates collagen-induced arthritis partially by inhibiting peripheral pro-inflammatory mediators. Exp Ther Med. 15(4): 4014-4018, 2018.

Kapoor, M.; Martel-Pelletier, J.; Lajeunesse, D.; Pelletier, J. P.; Fahmi, H. Role of proinflammatory cytokines in the pathophysiology of osteoarthritis. Nature Reviews Rheumatology. Jan. 7 (1): 33, 2011.

Lee, K.; Seo, I.; Choi, M. H.; Jeong, D. Roles of Mitogen-Activated Protein Kinases in Osteoclast Biology. Int J Mol Sci. 19(10): 3004, 2018.

Machado, A.; Liria, C. W.; Proti, P. B.; Remuzgo, C.; Miranda, M. Chemical and enzymatic peptide syntheses: basic aspects and applications, Quim Nova, vol. 27, No. 5, 781-789, 2004.

Mant, C. T.; Hodges, R.S. High-performance Liquid Chromatography of Peptides and Proteins: Separation, Analysis, and Conformation, CRC Press Inc.: Boca Raton, 1991.

Mosmann, T. Rapid Colorimetric Assay for Cellular Growth and Survival: Application to Proliferation and Cytotoxicity Assays. Journal of Immunological Methods; v. 65, n 1-2, p. 55-63, 1983.

Ni, Z., Kuang, L., Chen, H., Xie, Y., Zhang, B., Ouyang, J., Wu, J., Zhou, S., Chen, L., Su, N., Tan, Q., Luo, X., Chen, B., Chen, S., Yin, L., Huang, H., Du, X., Chen, L. The exosome-like vesicles from osteoarthritic chondrocyte enhanced mature IL-1β production of macrophages and aggravated synovitis in osteoarthritis. Cell Death Dis. 10(7): 522, 2019.

Perrot, S. Osteoarthritis pain. Best Practice & Research Clinical Rheumatology, v. 29, n. 1, p. 90-97, 2015.

Reis, C. V.; Portaro, F. C. V.; Andrade, S. A.; Fritzen, M.; Fernandes, B.; Sampaio, C. A. M.; Camargo, A. C. M. & Chudzinski-Tavassi, A. M. A Prothrombin Activator Serine Protease from the *Lonomia obliqua* Caterpillar Venom (Lopap): Biochemical Characterization. Thromb. Res. 102: 427-36, 2001a.

Reis, C. V., Farsky, S. H. P., Fernandes, B. L., Santoro, M. L., Oliva, M. L. V., Mariano, M., Chudzinski-Tavassi, A. M. In Vivo Characterization of Lopap, a Prothrombin Activator Serine Protease from the *Lonomia obliqua* Caterpillar Venom. Thromb. Res. 102:437-43, 2001b.

Sprouse-Blum, A. S.; Smith, G.; Sugai, D.; Parsa, F. D. Understanding Endorphins and their Importance in Pain Management. Hawaii Med J. 69(3): 70-1, 2010.

Zannin, M.; Lourenço, D. M.; Motta, G.; Dalla Costa, L. R.; Grando, M.; Gamborje, G.; Noguti, M. A. & Chudzinski-Tavassi, A. M. Blood coagulation and fibrinolytic factors in 105 patients with hemorrhagic syndrome caused by accidental contact with *Lonomia obliqua* caterpillar in Santa Catarina, southern Brazil. Thromb. Haemost. 89:355-364, 2003.

Zhou, P. H.; Liu, S. Q; Peng, H. The Effect of Hyaluronic Acid on IL-1β-Induced Chondrocyte Apoptosis in a Rat Model of Osteoarthritis. Journal of Orthopedic Research, Dec. 2008, pp. 1643-1648.

Mashaghi et al., "Neuropeptide substance P and the immune response", Cellular and Molecular Life Sciences, DOI 10.1007/s00018-016-2293-z, published online Jun. 17, 2016, Springer International Publishing 2016.

Guidotti et al., "Cell-Penetrating Peptides: From Basic Research to Clinics", Trends in Pharmacological Sciences, Apr. 2017, vol. 38, No. 4, http://dx.doi.org/10.1016/j.tips.2017.01.003.

Batista et al., "A new Factor Xa inhibitor from *Amblyomma cajennense* with a unique domain composition", Archives of Biochemistry and Biophysics 493 (2010) 151-156.

Agholme et al., "An In Vitro Model for Neuroscience: Differentiation of SH-SY5Y Cells into Cells with Morphological and Biochemical Characteristics of Mature Neurons", Journal of Alzheimer's Disease 20 (2010) 1069-1082.

Yang et al., "Daidzein induces neuritogenesis in DRG neuronal cultures", Journal of Biomedical Science 2012, 19:80, http://www.jbiomedsci.com/content/19/1/80.

Twentyman & Luscombe, "A study of some variables in a tetrazolium dye (MTT) based assay for cell growth and chemosensitivity", Br. J. Cancer (1987), 56, 279-285.

Reis et al., "Lopap, a prothrombin activator from *Lonomia obliqua* belonging to the lipocalin family: recombinant production, biochemical characterization and structure-function insights", Biochem J. (2006) 398, 295-302, doi: 10.1042/BJ20060325.

International Search Report (English and Portuguese) and Written Opinion of the ISA (Portuguese) issued in PCT/BR2020/050360, mailed Oct. 5, 2021; ISA/EP.

Chudzinski-Tavassi, Ana Marisa et al., "A lipocalin sequence signature modulates cell survival", FEBS Letters 585 2896-2900, (2010).

Wilan, Luana et al., "Wound Healing Effects of a Lipocalin-Derived Peptide", Journal of Clinical Toxicology,vol. 4, Issue 2, DOI: 10.4172/2161-0495.187, (2014).

Wan Tan, Yih et al., "Structures of Two Major Allergens, Bla g 4 and Per a 4, from Cockroaches and Their IgE Binding Epitopes", The Journal Of Biological Chemistry, vol. 284, No. 5, pp. 3148-3157, Jan. 30, 2009.

European Office Action from counterpart EP208030783, dated Feb. 14, 2025.

Blast—Evidence Supporting Art. 10 (IX) for Brazilian Office Action dated Jan. 6, 2026 for Brazilian Patent Application BR102019018666-6.

Relatório de Busca, Relatório de Exame Técnico e Parecer [Search Report, Technical Examination Report and Opinion] Dated Jan. 6, 2026 From the Serviço Público Federal, Ministério do Desenvolvimento, Indústria, Comércio e Serviços, Instituto Nacional da Propriedade Industrial do Brasil Re. Application No. BR102019018666-6 and Its Machine Translation Into English. (18 Pages).

(56) References Cited

OTHER PUBLICATIONS

Alvarez-Flores et al. "Losac, the First Hemolin That Exhibits Procogulant Activity Through Selective Factor X Proteolytic Activation", The Journal of Biological Chemistry, 286(9): 6918-6928, Published Online Dec. 22, 2010.

Bosch et al. "Hemolin Triggers Cell Survival on Fibroblasts in Response to Serum Deprivation by Inhibition of Apoptosis", Biomedicinc & Pharmacotherapy, 82: 537-546, Published Online Jun. 6, 2016.

* cited by examiner

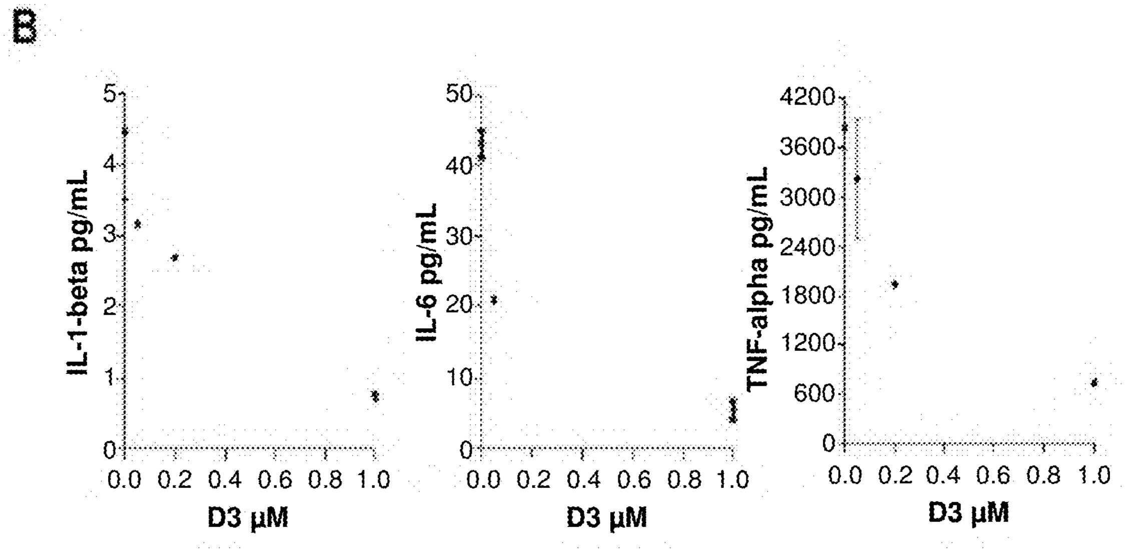
Figure 4 (continuation)

(Continuation)

ANTI-INFLAMMATORY PEPTIDES, PHARMACEUTICAL COMPOSITION CONTAINING SUCH PEPTIDES AND USES THEREOF

CROSS-REFERENCE TO RELATED APPLICATIONS

This application is a U.S. National Phase Application under 35 U.S.C. 371 of International Application No. PCT/BR2020/050360, filed on Sep. 9, 2020, which claims the benefit of Brazilian Patent Application No. 10 2019 018666 6, filed on Sep. 9, 2019. The entire disclosures of the applications referenced above are incorporated herein by reference.

FIELD OF THE INVENTION

The present invention relates to various sequences of new peptides and derivatives with anti-inflammatory effects in various cellular models (macrophages derived from THP-1, neurons, osteoclasts, and chondrocytes), in the context of stimulus-induced inflammation widely known in the literature for each model. The compounds were shown to be able to reverse the expression of molecules associated with the cell's inflammatory mechanism, in addition to inducing regenerative proteins and reducing pain markers. Accordingly, the compound claimed in the present invention can be applied to degenerative diseases of an inflammatory nature including rheumatoid arthritis and osteoarthritis.

BACKGROUND OF THE INVENTION

Osteoarthritis (OA) is a degenerative joint disease characterized by the degradation of the extracellular matrix (ECM) and the chondrocytes present in the cartilage (KAPOOR et al., 2011). In patients who developed the disease, there is an increase in inflammatory mediators in synovial fluid, such as interleukins and nitric oxide (NO), which induce chondrocyte apoptosis (ZHOU et al., 2008 & KAPOOR et al., 2011 & AKKIRAJU; NOHE, 2015). Chondrocytes have receptors for ECM components (GOLDRING & OTERO, 2011), and this interaction between ECM and chondrocytes has a regulatory function that ensures cell survival, and when deregulated is capable of causing pain in patients since it leads to the loss of ECM and chondrocytes, in addition to the release of NO (PERROT, 2015). The existing treatments do not reverse the disease status (AKKIRAJU; NOHE, 2015). Therefore, studies on new molecular targets are needed to find a new treatment for OA.

*Lonomia obliqua* is a Brazilian caterpillar known to cause hemorrhagic syndrome in patients who have had contact with its bristles (ZANNIN et al., 2003).

Some studies have identified the proteins responsible for the changes in blood clotting presented in patients. Interestingly, in addition to modulating blood coagulation, some of these molecules modulate the mechanisms of inflammation and cell survival when studied in vitro in cell models, having the ability to reduce cell death from stress induced by serum deprivation (ALVAREZ-FLORES et al., 2006, 2011; FRITZEN et al., 2005; REIS et al., 2001a, 2001b, REIS et al., 2006). These molecules have been extensively studied (structurally and functionally). These studies led to the design of smaller peptide entities that have anti-apoptotic activity, without pro-coagulant effects. The peptides corresponding to several conserved motifs, with or without changes in the sequences, corresponding to the cytoprotective molecules of the secretions of the *Lonomia obliqua* caterpillar.

Macrophages are cells of the immune system that have functions of phagocytosis and presentation of antigens. Macrophages produce inflammatory mediators and destructive responses during the osteoarthritis process (NI et al., 2019). Considering that the injury process involves the inflammatory response, several anti-inflammatory screening models have been established, such as macrophages derived from the THP-1 strain.

Osteoclasts are multinucleated cells formed from cells of the monocyte/macrophage lineage, and their differentiation and function are regulated by various cytokines, hormones, and growth factors. In particular, the macrophage colony-stimulating factor (M-CSF), and the receptor activator for nuclear factor k-B ligand (RANKL) are essential in the regulation of the sequential osteoclast genesis process, including the proliferation of osteoclast precursors, adhesion, cell-cell migration, and fusion to form multinucleated cells, as well as in the migration, survival and bone resorption function of mature osteoclasts (LEE et al., 2018).

The Substance P (SP) is a peptide mainly secreted by neurons and is involved in many biological processes, including nociception (pain transmission process) and neurogenic inflammation (MASHAGHI et al., 2016).

β-endorphins are neuropeptides involved in pain control, having effects similar to morphine, and capable of suppressing inflammation and reducing the production of pro-inflammatory mediators in arthritis-induced inflammatory pain (Sprouse-Blum et al., 2010; HE et al., 2018).

Thus, studies carried out on this invention have made it possible to determine several synthetic peptides with activity both in cell remodeling and in reducing inflammation and pain markers that make them candidates for new treatments, which are more specific and efficient for degenerative diseases of an inflammatory nature.

BRIEF DESCRIPTION OF THE DRAWINGS

The structure and operation of the present invention, together with additional advantages thereof, can be better understood by reference to the attached drawings and the following description.

Figure 4:
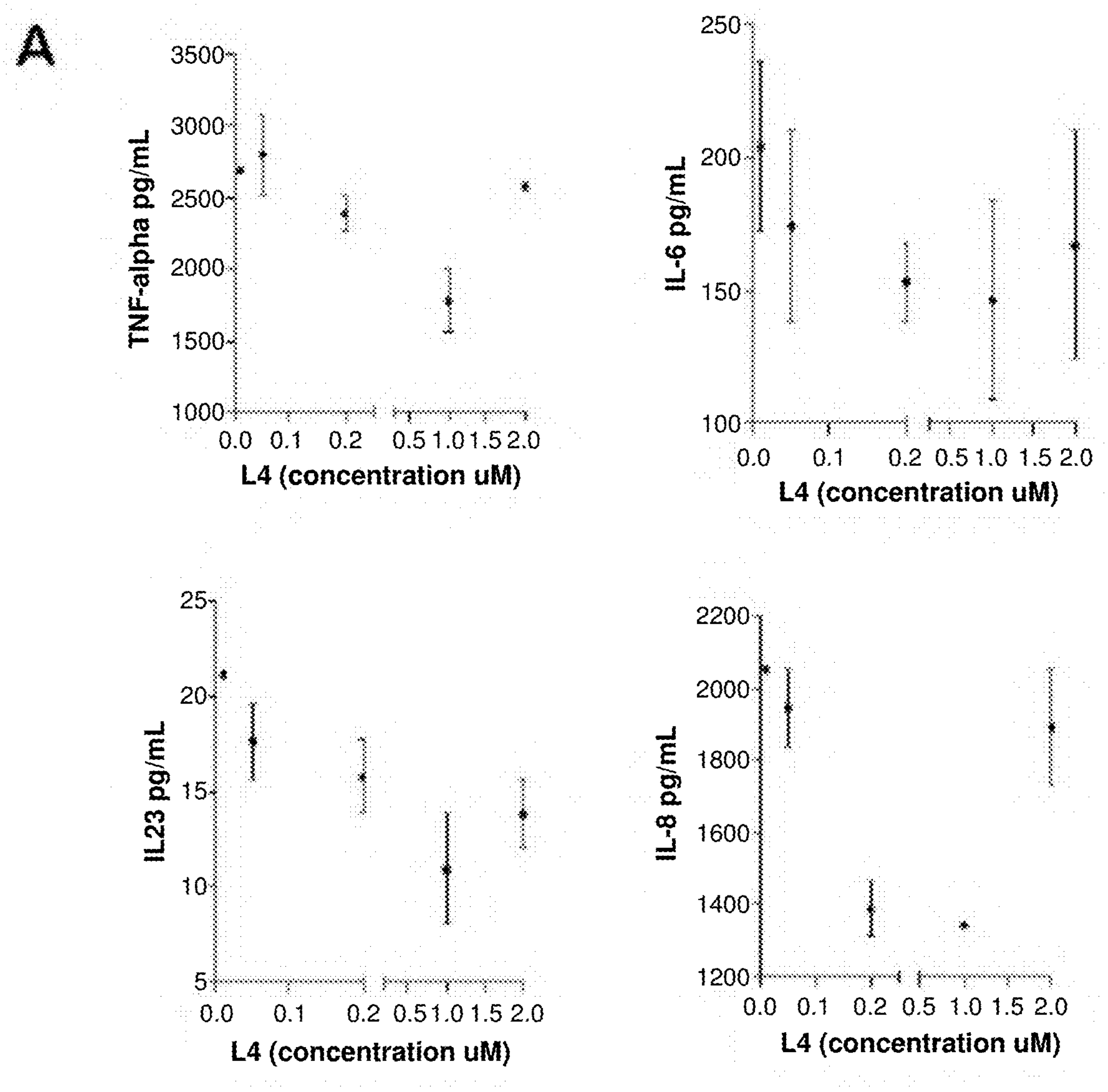
Figure 5:
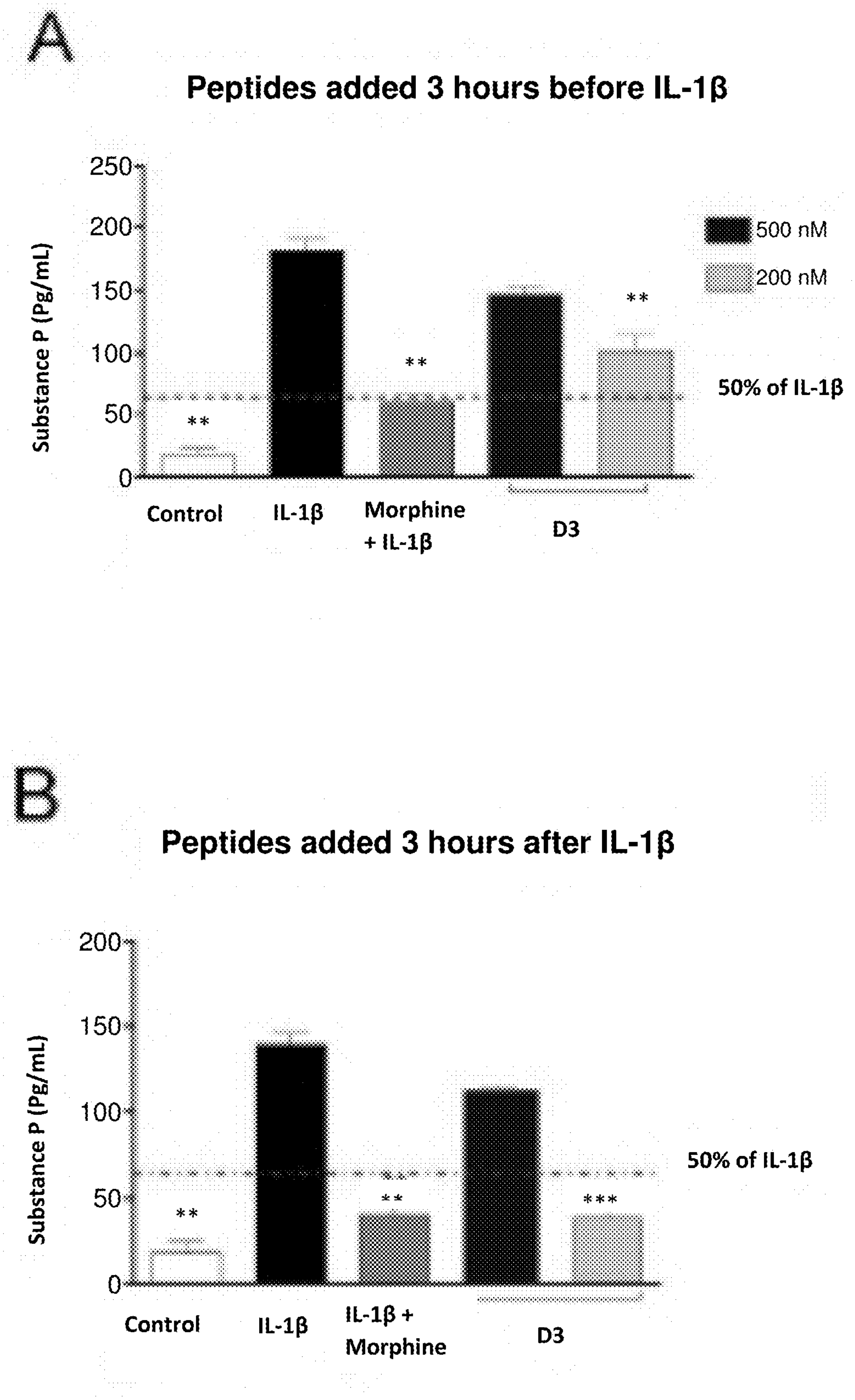
Figure 5:
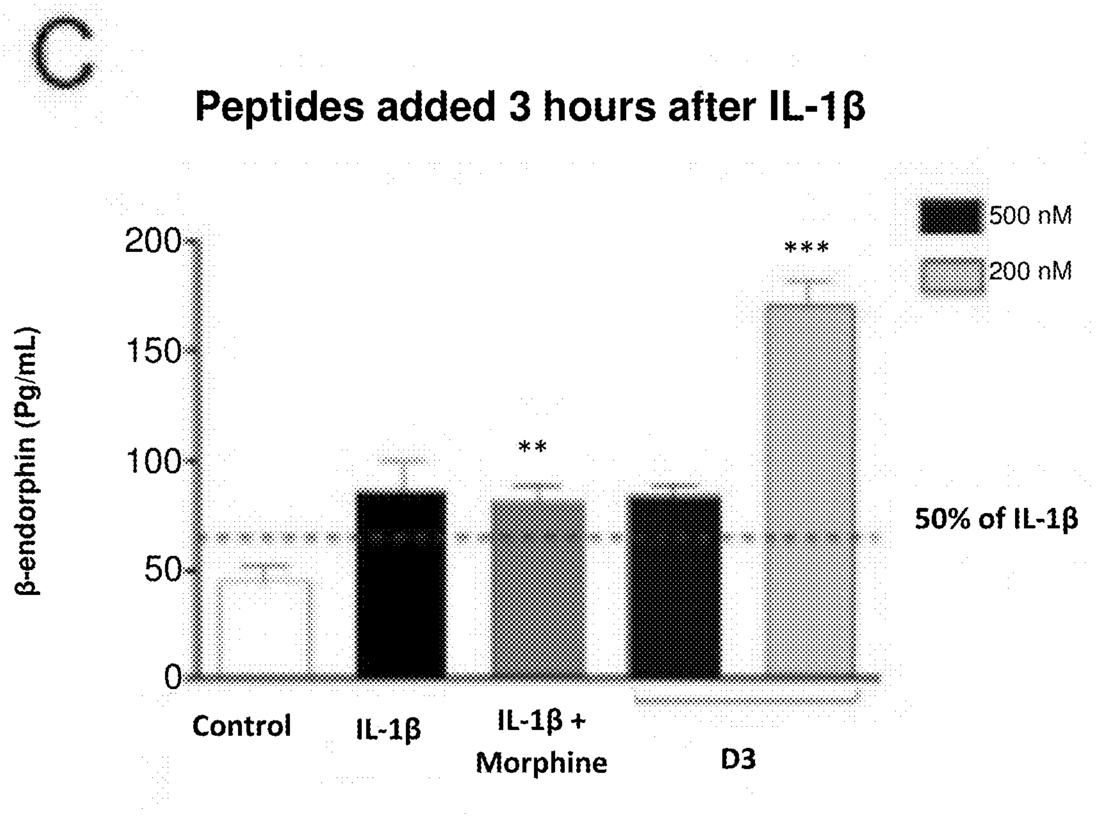
Figure 6:
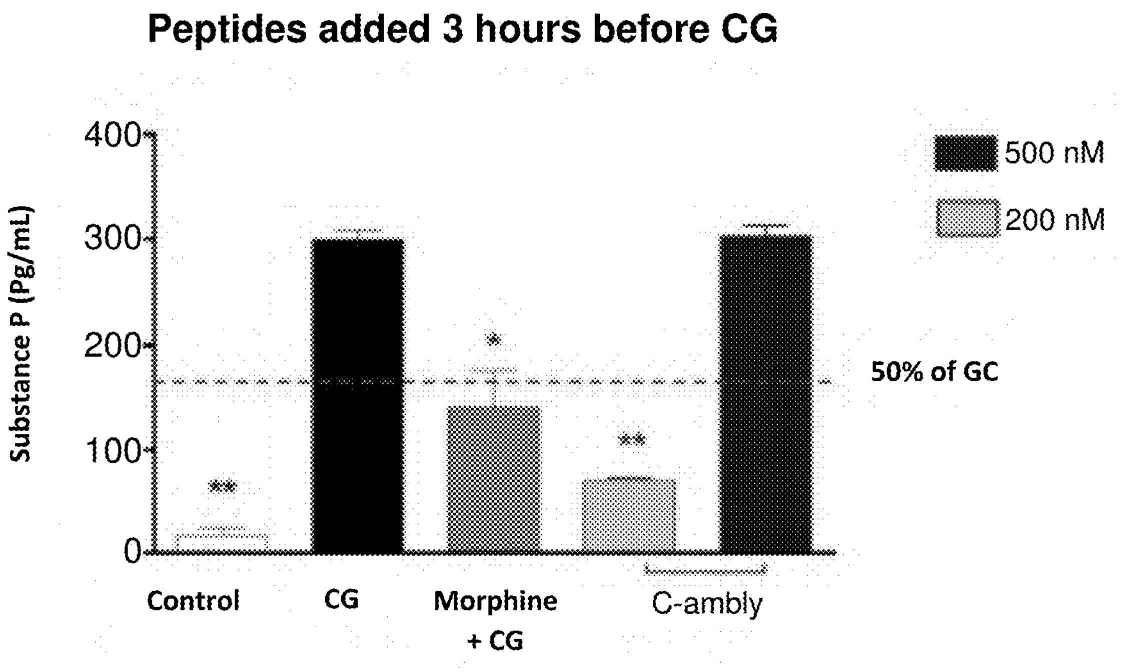
Figure 7:
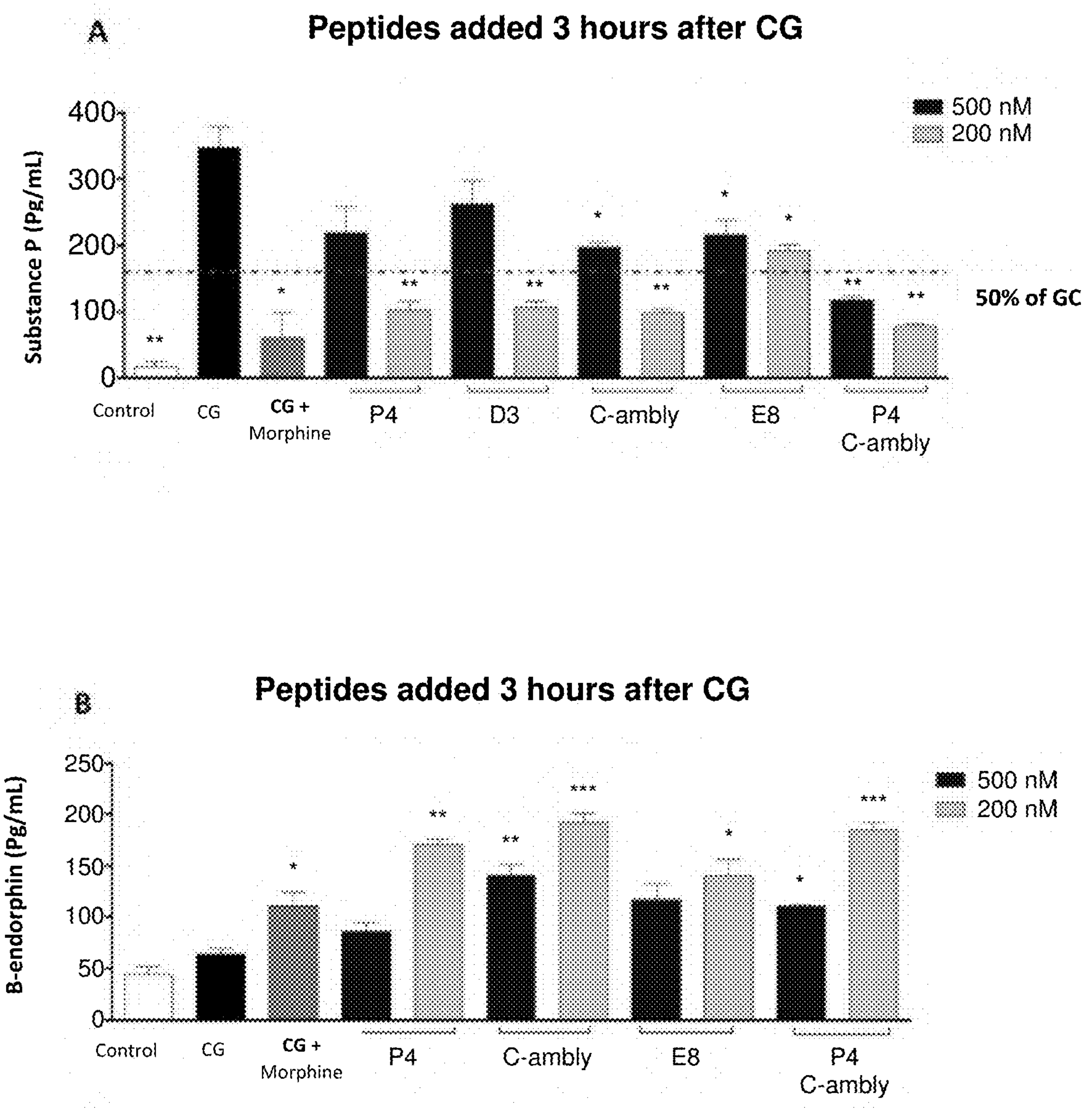
Figure 8:
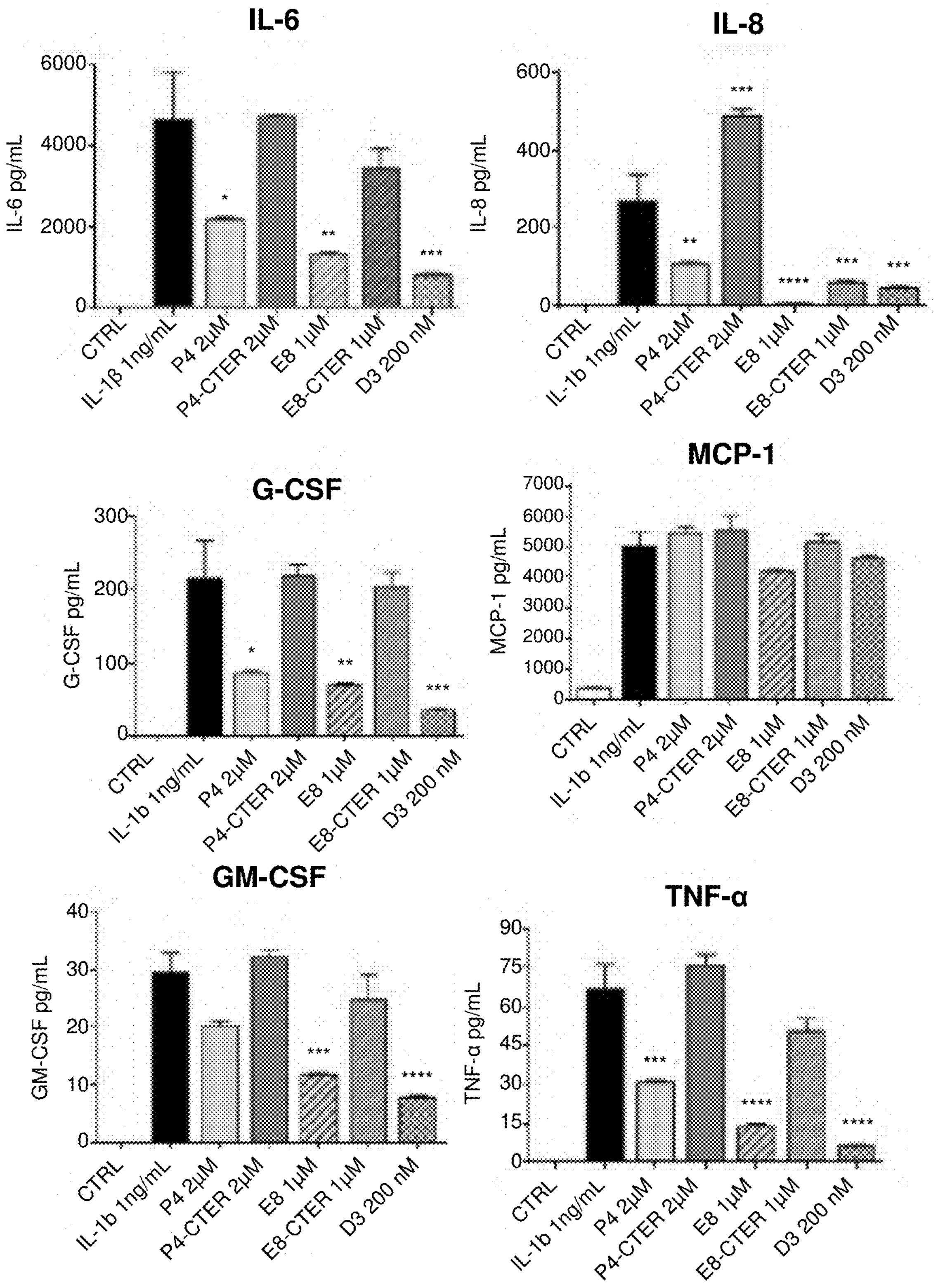

(C) and IL-10 (D) using a multiplex kit. * p<0.05 vs. LPS;  p<0.01 vs. LPS; * p<0.005 vs. LPS;

FIG. 4 shows the Dose-Response Effect of L4 and D3 peptide on the production of inflammatory cytokines. THP-1 cells differentiated into macrophages were induced with LPS (10 ng/mL) and, one hour later, treated with L4 or D3 peptide (0.05 μM, 0.2 μM, 1 μM, and 2 μM). After 24 hours, the culture medium was collected and TNF-alpha, IL-6, IL-23, and IL-8 were measured by Multiplex. (A) L4 peptide. (B) D3 peptide;

FIG. 5 shows: (A) production of Substance P in neurons incubated with D3 peptide (200 nM and 500 nM) 3 hours before incubation with IL-1β (10 ng/mL); (B) Production of Substance P in neurons incubated with peptide D3 (200 nM and 500 nM) 3 hours after incubation with IL-1β (10 ng/mL); (C) production of β-endorphin in neurons incubated with peptides 3 hours after incubation with IL-1β (10 ng/mL). ANOVA and Dunnet  p<0.01, * p<0.001 compared to IL-1β;

FIG. 6 shows the production of substance P in neurons incubated with the Cambly peptide (200 nM and 500 nM) 3 hours before incubation with glycated collagen (GC). ANOVA and Dunnet * p<0.05; ** p<0.01 compared to glycated collagen (GC);

FIG. 7 shows: (A) production of Substance P; and (B) production of β-endorphin in neurons incubated with peptides 3 hours after incubation with glycated collagen (GC). ANOVA and Dunnet * p<0.05  p<0.01, * p<0.001 compared with GC;

FIG. 8 shows the effect of peptides on the release of 6 analytes in the pro-inflammatory model of chondrocytes treated with IL-1β (1 ng/mL). Values were obtained from each analyte in pg/mL from treatment with the peptides in the presence of IL-1β (1 ng/mL). The data are presented as the mean±MSE (* p<0.05 when compared to the control with IL-1β, test t, n=3).

Figure 9:
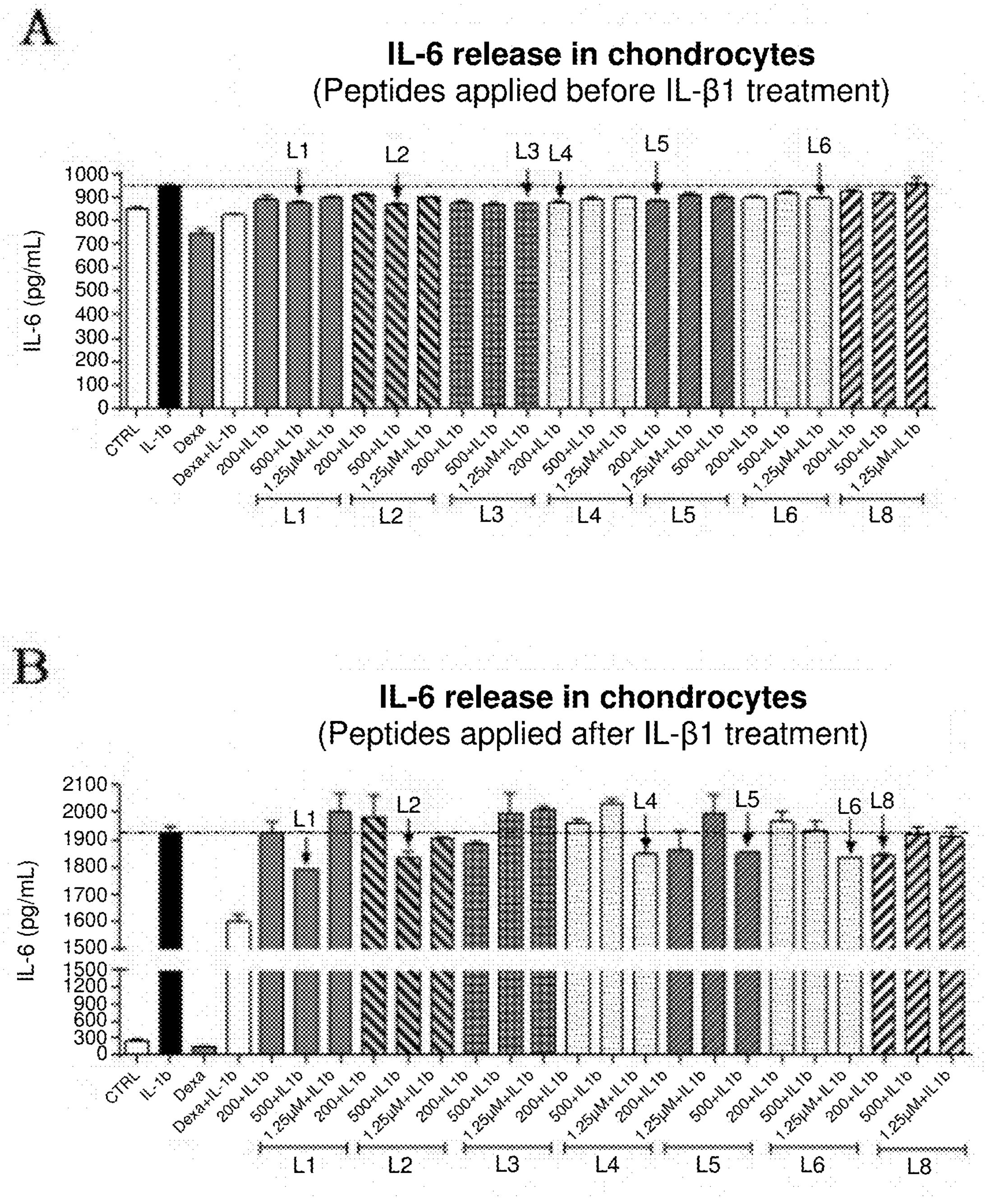

FIG. 9 shows the effect of synthetic peptides on IL-6 release in the pro-inflammatory model of chondrocytes treated with IL-1β (A) chondrocytes were pretreated with peptide (200 nM, 500 nM, and 1.25 μM) for 1 hour before the addition of IL-1β (1 ng/mL) and an additional incubation of 24 hours before the collection of supernatants. (B) Chondrocytes were pretreated for 1 hour with IL-1β (1 ng/mL) before the addition of peptides (200 nM, 500 nM, and 1.25 μM) and an additional incubation of 24 hours before collecting the supernatants.

DETAILED DESCRIPTION OF THE INVENTION

To solve the problems mentioned above, the present invention will provide significant advantages over the use of various sequences of new peptides and derivatives with anti-inflammatory effects in various cellular models (chondrocytes, osteoclasts, macrophages derived from THP-1, and neurons), in the context of stimulus-induced inflammation widely known in the literature for each model. Thus, enabling an increase in its performance and presenting a more favorable cost/benefit ratio.

Material and Methods

Peptides

The present peptides can be chemically synthesized by standard methods of chemical synthesis widely known, including the solid phase methodology that uses polymeric supports, such as a p-methyl-benzhydryl amine resin (MBHA) for synthesis by the t-Boc or F-moc strategy (MACHADO et al., 2004). The peptides can also be biologically synthesized by recombinant DNA technology using, for example, an expression vector containing a nucleic acid sequence encoding one of the peptides described in the present invention. After synthesis, the peptides can be purified by known methods, including high-performance liquid chromatography (HPLC), with reverse phase (RP-HPLC) being the preferred technique (MANT & HODGES, 1991), using a linear gradient of 1% trifluoroacetic acid (TFA) in acetonitrile and water. The purified peptides can be analyzed for their chemical homogeneity by amino acid analysis (MACHADO et al., 2004).

TABLE 1

List of synthetic peptides and sequences thereof.

| Compound | Molecular Mass | Sequence | SEQ ID NO: | Number of amino acids |
|---|---|---|---|---|
| D3 | 1271.3 | DYWHDGHDLN | 1 | 10 |
| L1 | 1132.3 | IWTKDGKAIT | 2 | 10 |
| L2 | 1198.3 | NYFKNGKDVN | 3 | 10 |
| L3 | 1201.5 | VWRKNGKKVS | 4 | 10 |
| L4 | 1202.4 | TWNKKGKKVN | 5 | 10 |
| L5 | 1292.5 | SWLKNGREFR | 6 | 10 |
| L6 | 1258.4 | QPEISWTRNK | 7 | 10 |
| L8 | 1257.4 | RWLKDGQAFH | 8 | 10 |
| P4 | 1310.5 | YAIGYSCKDYK | 9 | 11 |
| E8 | 824.9 | YSIVAGCL | 10 | 8 |
| Cambly | 5856.4 | EEQTHFHFESPKLISFKVQDYWILNDIMKKNLTGISLKSEEEDADSGEID | 11 | 50 |
| E8-Cambly | 6875.5 | YSIVAGSLGGGGEEQTHFHFESPKLISFKVQDYWILNDIMKKNLTGISLKSEEEDADSGEID | 12 | 62 |
| P4-Cambly | 7360.9 | YAIGYSSKDYKGGGGEEQTHFHFESPKLISFKVQDYWILNDIMKKNLTGISLKSEEEDADSGEID | 13 | 65 |

Cell Cultivation

The present invention includes the culture of monocytic cells of human leukemia (THP-1), osteoclast, primary human blood-derived mononuclear cells (PBMNC), and human chondrocytes (NHAC-kn).

The cells were grown in a specific culture medium according to their characteristics and needs at 37° C. in an incubator containing 5% $CO_2$.

Differentiation of THP-1 in Macrophages

Macrophages were obtained from the differentiation of monocytes THP-1. Briefly, $1\times10^7$ cells were treated in the RPMI medium with 25 nM PMA for 48 hours followed by 24 hours of rest in medium without PMA. Subsequently, the cells were released and plated for the respective treatments.

Neuronal Differentiation Obtained from SHSY5Y Cells

The differentiation process consists of 6 stages distributed over 7 days. On the first day of the differentiation protocol (day 0), cells were seeded in collagen-coated plates. On days 1, 3, and 4 the culture medium was removed, and the differentiation medium containing 2% fetal bovine serum (FBS) and retinoic acid (RA) 10 μM) was added. On day 5, the medium was removed and the culture was incubated with culture medium and brain-derived neurotrophic factor (BDNF) (50 ng/mL). On day 7 of the differentiation process, differentiated neurons are fully ready for use (Agholme et al., 2010, with some modifications).

Osteoclasts Cultivation

Experimental Model

Figure 1:
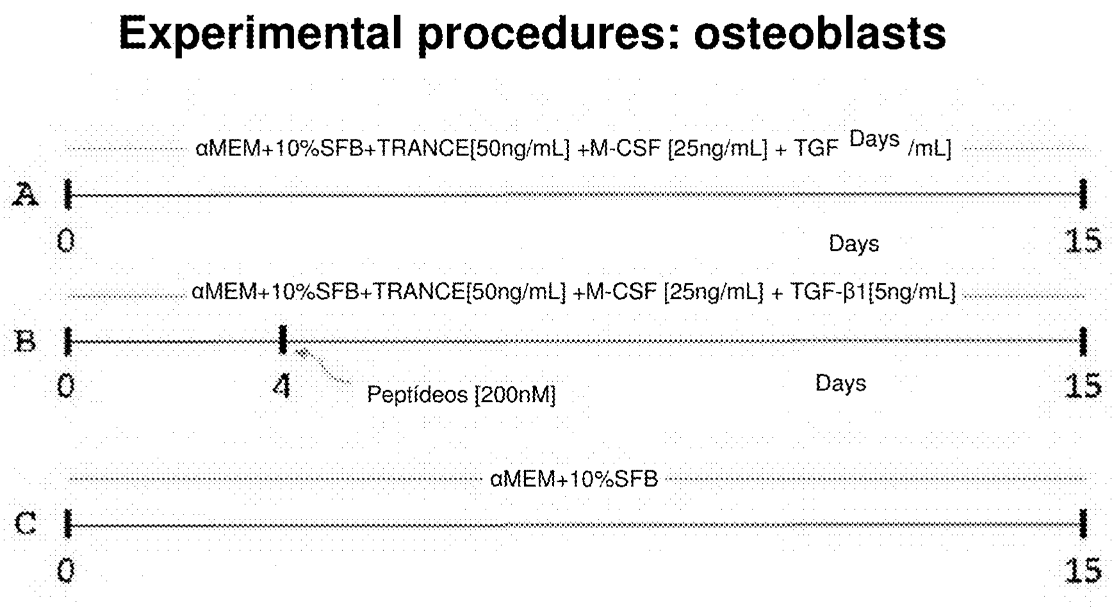
FIG. 1 shows an experimental design of the osteoclast differentiation model and the screening of anti-inflammatory peptides. A. Positive differentiation controls. B. Influence of synthetic peptides (200 nM) on osteoclast differentiation. C. Negative differentiation control. αMEM—Minimum Essential Medium Eagle Alpha Modification; FBS—fetal bovine serum; TRANCE—Tumor Necrosis Factor (TNF)-related Activation-induced Cytokine; M-CSF—Macrophage Colony-Stimulating Factor; TGF-β1—Transforming growth factor beta-1.

FIG. 1 shows an experimental model of osteoclast differentiation for the screening of synthetic peptides A. Positive controls and C. Negative differentiation controls. B. Influence of synthetic peptides (200 nM) on osteoclast differentiation.

Chondrocyte Cultivation

The primary human chondrocytes used in this assay were purchased from Lonza: Normal Human Articular Primary chondrocytes (NHAC-Kn, #CC-2550, Lot 8F3336). Chondrocyte cell culture was performed in bottles (Sarstedt T175 and T75). The cells were cultivated in DMEM culture medium (Sigma) supplemented with 10% fetal bovine serum (FBS) (Sigma), incubated in an oven at 37° C. and 5% $CO_2$, and cultures were used in the sixth passage. The culture medium was changed every two days until the culture reached 80% confluence.

Cell Viability

The evaluation of metabolically active cells was performed using the colorimetric assay of [3-(4,5-dimethylthiazol-2-yl)-2,5-diphenyl tetrazolium] bromide (MTT, Sigma-Aldrich, St. Louis, USA), as previously reported (Twentyman et al., 1987). After each incubation period, the supernatant was removed and a MTT solution (0.5 mg/mL in phosphate-buffered saline—PBS) was added, and the cells incubated at 37° C. and 5% $CO_2$ for 3 hours (Yang et al., 2012). After this period, the solution was removed and crystals of dark blue formazan were solubilized with 1 mL of dimethyl sulfoxide (DMSO, Merck, Darmstad) for 5 minutes. Quantification of formazan was done using an automatic ELISA microplate reader (SLT, Austria) at 570 nm.

Anti-Nociceptive/Anti-Inflammatory Model $7\times10^3$ neurons/well were incubated with 10 μM of morphine (inhibitory response control) or peptides (200 nM and 500 nM) 3 hours before or 3 hours after incubation with IL-1β (10 ng/mL) or glycated collagen (GC) (100 μg/mL) (both positive controls for the release of substance P). After 24 hours of incubation, the cell viability assay and the detection of substance P and β-endorphin in the supernatant were performed.

Multiplex with Magnetic Spheres (MILLIPLEX® MAP Magnetic Bead Panel)

The kit is based on Luminex® xMAP® technology that allows the simultaneous analysis of various cytokines. The technique is based on marked magnetic fluorescent spheres, known as MagPlex®-C microspheres. These microspheres are covered with capture antibodies specific for IL-6 myokines, and specifically capture the analyte in the supernatant. Each microsphere was individually identified and the results were analyzed using Luminex® Xponent® 4.2 acquisition software.

TRAP+ Cell Count

PBMNC were isolated and, immediately after, plating inductive culture medium (composed of Alpha-MEM+10% FBS+MCSF [25 ng/mL]+RANKL [50 ng/mL]+TGF-beta 1 [5 ng/mL]+Dexamethasone [1 μM]) was added for 15 days. On day four, the *L. obliqua* venom at a concentration of 0.5/mL or toxins at a concentration of 200 nM, each individually, was added to the osteoclast precursor culture and these culture conditions were maintained until the end of the differentiation. Then, the cells were fixed and stained with tartrate-resistant acid phosphatase (TRAP).

Results

Osteoclast

TRAP+ Cells Count

FIG. 1 shows an experimental design of the osteoclast differentiation model and the screening of anti-inflammatory peptides.

Figure 2:
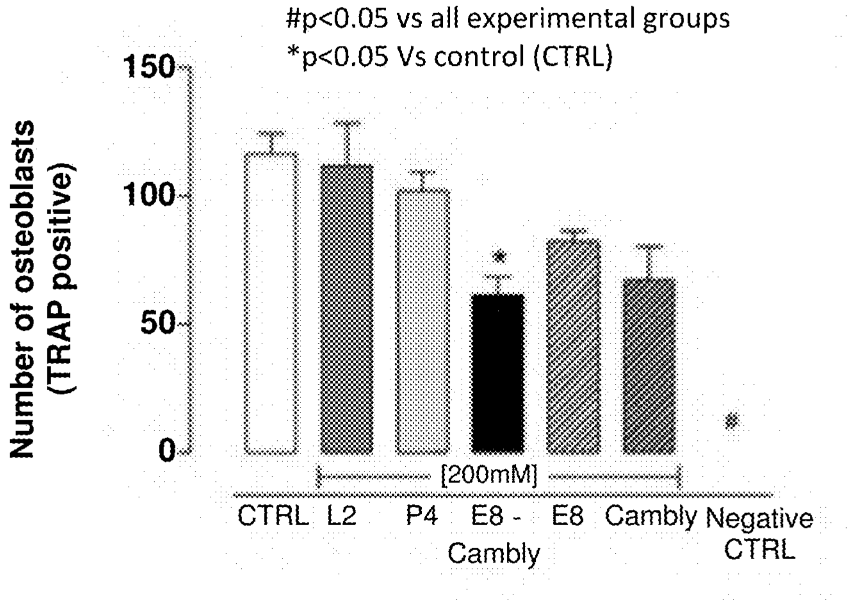
FIG. 2 shows the number of TRAP-positive cells observed after treatments with synthetic peptides in comparison with positive and negative controls for osteoclast differentiation.

FIG. 2 shows the count of TRAP-positive cells observed after the peptide treatments. Using statistical analysis, the number of TRAP+ cells after the incubation of osteoclast precursors with synthetic peptides was evaluated. FIG. 2 shows the summary data from three independent experiments. L2 and P4 showed no statistically significant difference in the number of TRAP+ cells, while a significant decrease in TRAP+ cells was observed after treatment with E8-Cambly when compared to the positive control (CTRL).

THP-1

THP-1 Multiplex

In the multiplex assay, D3 and L4 peptides showed an anti-inflammatory effect on all inflammatory cytokines tested, significantly reducing the levels of IL-1β, IL-6, and TNF-α when compared to the group treated only with LPS. If, on the one hand, D3 also reduced levels of IL-10, the only anti-inflammatory cytokine tested, L4 promoted an increase in this cytokine (FIG. 3).

Figure 3:
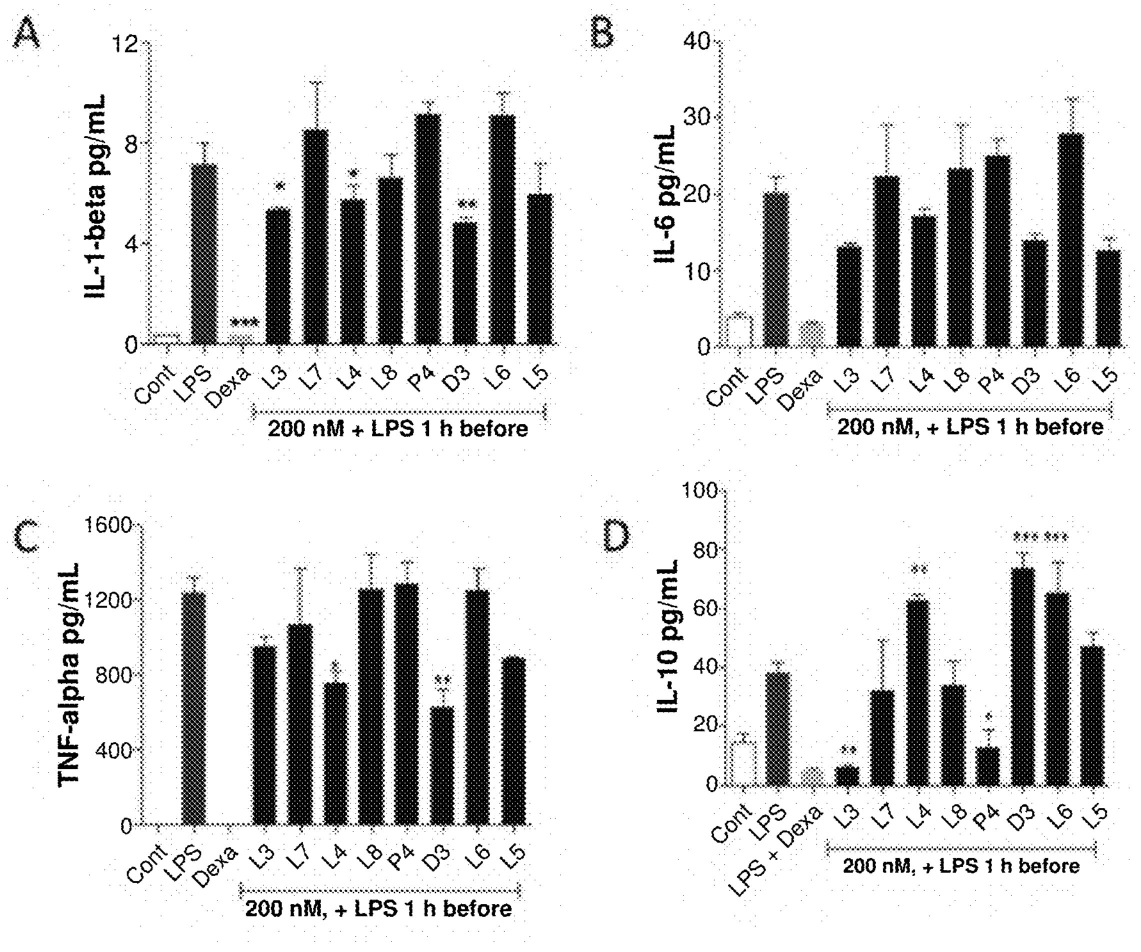
FIG. 3 shows the anti-inflammatory effects of synthetic peptides on the production of inflammatory cytokines (IL-1-beta, IL-6, and TNF-alpha) and the anti-inflammatory cytokine IL-10. THP-1 cells differentiated into macrophages were induced with LPS (10 ng/mL) and 1 h later treated with synthetic peptides at a concentration of 200 nM. Dexamethasone (10 μM), an inflammation inhibitor, was used as a control. After 24 h, the culture medium was collected for measurement of the cytokines IL-1ß (A), IL-6 (B), TNF-α

FIG. 3 shows the anti-inflammatory effects of the synthetic peptide in the production of inflammatory (IL-1β, IL-6, and TNF-α) and anti-inflammatory (IL-10) cytokines. THP-1 cells differentiated into macrophages were induced with LPS (10 ng/mL) and, one hour later, treated with synthetic peptides, 200 nM dexamethasone (inflammation inhibitor, 10 μM). After 24 hours, the culture medium was collected and IL-1β (A), IL-6 (B), TNF-α (C), and IL-10 were measured by Multiplex. * $p<0.05$ vs. LPS;  $p<0.01$ vs. LPS; * $p<0.005$ vs. LPS.

The peptides with the most promising anti-inflammatory effects, D3 and L4, were then tested on a dose-response curve. The 200 nM dose of L4 was enough to achieve the greatest inhibition in the release of inflammatory cytokines concerning IL-6 and IL-8, while 1 μM was the most effective dose concerning TNF-α and IL-23 (FIG. 4). Regarding the release of cytokines tested with D3, the best dose, in all cases, was 1 μM (FIG. 4). Both L4 and D3 reduced the production of inflammatory cytokines in response to LPS in a dose-dependent way.

FIG. 4 shows the dose-response effect of L4 and D3 peptide on the production of inflammatory cytokines. THP-1 cells differentiated into macrophages were induced with LPS (10 ng/mL) and, one hour after, treated with L4 (0.05 μM, 0.2 μM, 1 μM, and 2 μM). After 24 hours, the culture medium was collected and TNF-α, IL-6, IL-23, and IL-8 were measured by Multiplex. (A) L4 peptide. (B) D3 peptide.

SH-SY5Y

Cell Viability and Production of Inflammatory/Nociceptive Mediators

Regarding cell viability, there was no cytotoxic effect of peptides on neurons. Considering IL-1β as a positive control, when peptides were added 3 hours before IL-1β, 200 nM of D3 peptide significantly inhibited the production of substance P induced by IL-1β (FIG. 5). No significant differences were detected in the production of β-endorphin. In the assays in which the peptides were added 3 hours after IL-1β, 200 nM of D3 was able to inhibit the production of substance P and induced the production of β-endorphin (FIG. 5).

FIG. 5 shows (A) production of Substance P in neurons incubated with peptides 3 hours before incubation with IL-1β; (B) Production of Substance P; (C) Production of β-endorphin in neurons incubated with peptides 3 hours after incubation with IL-113. ANOVA and Dunnet  $p<0.01$, * $p<0.001$ compared to Using the glycated collagen (GC) matrix as a positive stimulus, when the peptides were incubated 3 hours before the GC, the Cambly peptide was able to significantly decrease the production of Substance P (FIG. 6), however, it did not affect the production of β-endorphin. On the other hand, when the peptides were incubated 3 hours after GC, 200 nM of P4, D3, Cambly, E8, and P4-Cambly, significantly inhibited the production of Substance P and increased the production of β-endorphin (FIG. 7A).

FIG. 6 shows the production of substance P in neurons incubated with peptides, 3 hours before incubation with GC. ANOVA and Dunnet * $p<0.05$; ** $p<0.01$ compared to GC.

FIG. 7 shows: (A) Production of Substance P; (B) Production of β-endorphin in neurons incubated with peptides, 3 hours after incubation with GC. ANOVA and Dunnet * $p<0.05$  $p<0.01$, * $p<0.001$ compared to GC.

Chondrocytes

Multiplex

The identification and quantitative analysis of the cytokines present in the peptide treatment supernatant were performed using the Luminex xMAP Milliplex MAP Human Cytokine/Chemokine Magnetic Bead Panel Catalog #HCYTOMAG-60K technology, according to the manufacturer's instructions.

Six analytes that demonstrated changes in the presence of cytokine IL-1β (1 ng/mL), some deserve to be highlighted since they also have their presence altered from the treatment with the peptides: G-CSF, GM-CSF, IL-6, IL-8, MCP-1, and TNF-α (FIG. 8).

This study identified several cytoprotective peptides with an anti-inflammatory effect. Among the peptides with anti-inflammatory activity are D3, P4, E8, L1, L2, L3, L4, L5, L6, and L8.

Hemopoietic CSF, granulocyte-macrophage CSF (GM-CSF), and granulocyte CSF (G-CSF) are cytokines that mediate clonal proliferation and differentiation of progenitor cells into mature macrophages and/or granulocytes. In rheumatoid disease, chondrocytes are known as a potential source of CSF. The present invention proposes that the production of chondrocytes in the CSF in response to IL-1, and the simultaneous destruction of cartilage by IL-1, could provide a mechanism for the chronic nature of rheumatoid arthritis.

FIG. 8 shows the effect of the peptides on the release of six analytes. Values were obtained from each analyte in pg/mL from treatment with the peptides in the presence of IL-1β (1 ng/mL). The data are presented as the mean±MSE (*$p<0.05$ when compared to the control with IL-1β, test t, n=3).

The P4-Cambly peptide is a hybrid molecule containing the 10 amino acid sequence of the P4 peptide and a 50 amino acid sequence known as Cambly or CTER. The peptide sequence called "CTER" corresponds to a peptide derived from the Amblyomin-X molecule (Batista et al., 2010) with characteristics of CPP (cell-penetrating peptides), known in the literature as molecules that transport a wide variety of biologically active conjugates ("charges") to cells (Guidotti et al., 2017). Thus, CPPs are an innovative way for a drug to reach intracellular targets, reducing concentrations that could be toxic. The patent for this sequence (CTER) and its use as a CPP is being developed.

Conclusions

THP-1: D3 and L4 peptides reduced the production of inflammatory cytokines in response to LPS and both acted in a dose-dependent way.

The P4 peptide has no effect on the viability of macrophages derived from THP-1. However, it has the ability to inhibit part of the LPS-stimulated activation suggesting an anti-inflammatory action.

SH-SY5Y Neurons: D3 and Cambly peptides inhibited the production of substance P when added before the positive stimulus.

D3, P4, E8, Cambly, P4-Cambly peptides inhibited the production of substance P and increased the production of β-endorphin when added after the positive stimulus (glycated collagen matrix).

Osteoclast: Cambly and E8-Cambly peptides reduced the number of TRAP+ cells.

Chondrocytes: The data of the present invention are aligned with other models, suggesting that P4, E8, and D3, as well as the L1, L2, L3, L4, L5, L6, and L8 derived peptides, are potential candidates for the search for new targets for inflammation.

The peptides tested in the THP-1, Synoviocytes, and Chondrocytes models showed a significant reduction in the production of important cytokines for the inflammation process of various inflammatory diseases, such as arthritis. Besides, the peptides were also able to decrease pain markers in the neuron model.

Pharmaceutical Composition

In another aspect of the present invention, the pharmaceutical compositions provided herein comprise said anti-inflammatory peptides and at least one pharmaceutically acceptable carrier.

The term "pharmaceutically acceptable carrier" includes, but is not limited to, any carrier that does not interfere with the effectiveness of the biological activity of the active ingredients and that is not toxic to the patient to whom it is administered. Examples of suitable pharmaceutical carriers are well known in the art and include phosphate-buffered saline solutions, water, emulsions, such as oil/water emulsions, various types of wetting agents, sterile solutions, etc. Such a carrier can be formulated by conventional methods and can be administered to the individual in the dose and therapeutic routines most appropriate to each case. Preferably, the compositions are sterile, but can also be prepared under aseptic conditions. These compositions can also contain adjuvants, preservatives, emulsifying agents, and dispersing agents. Pharmaceutical formulations can be for a human, and/or veterinary/animal use. The formulations may be prepared in the form of particulate systems such as microparticles, nanoparticles, microspheres, nanospheres, liposomes, in carrier complexes as in cyclodextrins (alpha, beta, and gamma); still in the form of controlled release. The formulations can be prepared by associating the peptides in the most appropriate proportions and doses/concentrations. The formulations can be in the form of creams, ointments, gels, adhesives, sprays, including nanotechnology-based formulations, or even through the association with other active principles of the same biological effect, or even through the association with antimicrobials, antifungals, etc.

The administration of the compositions of the present invention can be carried out in different pathways, for example, intravenous, subcutaneous, intramuscular, topical or intradermal, particularly, the main ones are cutaneous, subcutaneous, topical, intradermal, rectal, intraocular, nasal, oral and auricular. The administration pathway, of course, depends on the type of treatment and the type of compound contained in the pharmaceutical composition. The dosage routines will be determined by the doctor and other clinical factors. As already well known in medical techniques, dosages for any patient depend on many factors, including the patient's weight, body area, age, sex, as well as pharmaceutical composition carrying the particular compound to be administered, time and administration pathway, type of therapy, general health status and other factors to be simultaneously considered.

Use of the Pharmaceutical Compositions of the Present Invention

The present invention also relates to the use of a synthetic peptide for the preparation of a pharmaceutical composition for cell remodeling, such as in reducing inflammation and in degenerative diseases of an inflammatory nature, in which the degenerative diseases of an inflammatory nature include rheumatoid arthritis and osteoarthritis.

The present invention also relates to the use of the synthetic peptide and/or pharmaceutical composition comprising said peptide as an agent that induces cell proliferation, preferably in tissue repair.

Thus, although only a few embodiments of the present invention have been shown, it will be understood that various omissions, substitutions, and changes in the pharmaceutical composition comprising the anti-inflammatory peptide and their uses can be made by a person skilled in the art, without departing from the spirit and scope of the present invention.

It is expressly provided that all combinations of elements that perform the same function in substantially the same way to achieve the same results are within the scope of the present invention. Substitutions of elements from one embodiment described to another are also fully intended and contemplated.

It is also necessary to understand that the drawings are not necessarily to scale, but that they have only a conceptual nature. Therefore, the intention is to be limited, as indicated by the scope of the attached claims.

REFERENCES

AKKIRAJU, H., NOHE, A. Role of Chondrocytes in Cartilage Formation, Progression of Osteoarthritis, and Cartilage Regeneration. Journal of developmental biology. 2015; 3: 177-192.

ALVAREZ-FLORES, M. P., FRITZEN, M., REIS, C. V., CHUDZINSKI-TAVASSI, A. M. Losac, a factor X activator from *Lonomia obliqua* bristle extract: its role in the pathophysiological mechanisms and cell survival. Biochem Biophys Res Commun. 2006 May 19; 343(4): 1216-23.

FRITZEN, M.; SCHATTNER, M.; RIBEIRO, A. L. Q.; BATISTA, I. F. C.; VENTURA, J.; PREZOTO, B. C. & CHUDZINSKI-TAVASSI, A. M. A prothrombin activator (Lopap) modulating inflammation, coagulation and cell survival mechanisms. Biochemical and biophysical research communications, v. 333, n. 2, p. 517-523, 2005.

GOLDRING, M. B.; OTERO, M. Inflammation in osteoarthritis. Current opinion in rheumatology, v. 23, n. 5, p. 471, 2011.

HE, X.; HUANG, L.; QIU, S.; YIN, X.; SHEN, Y.; WU, Y.; JIANG, Y.; FANG, J. β-Endorphin attenuates collagen-induced arthritis partially by inhibiting peripheral pro-inflammatory mediators. Exp Ther Med. 15(4): 4014-4018, 2018.

KAPOOR, M.; MARTEL-PELLETIER, J.; LAJEUNESSE, D.; PELLETIER, J. P.; FAHMI, H. Role of proinflammatory cytokines in the pathophysiology of osteoarthritis. Nature Reviews Rheumatology. January. 7 (1): 33, 2011.

LEE, K.; SEO, I.; CHOI, M. H.; JEONG, D. Roles of Mitogen-Activated Protein Kinases in Osteoclast Biology. Int J Mol Sci. 19(10): 3004, 2018.

MACHADO, A.; LIRIA, C. W.; PROTI, P. B.; REMUZGO, C.; MIRANDA, M. Chemical and enzymatic synthesis of peptides: basic principles and applications. New Chemistry. 24(5): 781-789, 2004.

MANT, C. T.; HODGES, R. S. High-performance Liquid Chromatography of Peptides and Proteins: Separation, Analysis, and Conformation, CRC Press Inc.: Boca Raton, 1991.

MOSMANN, T. Rapid colorimetric assay for cellular growth and survival: application to proliferation and cytotoxicity assays. Journal of Immunological Methods; v. 65, n 1-2, p. 55-63, 1983.

NI, Z., KUANG, L., CHEN, H., XIE, Y., ZHANG, B., OUYANG, J., WU, J., ZHOU, S., CHEN, L., SU, N., TAN, Q., LUO, X., CHEN, B., CHEN, S., YIN, L., HUANG, H., DU, X., CHEN, L. The exosome-like vesicles from osteoarthritic chondrocyte enhanced mature IL-1β production of macrophages and aggravated synovitis in osteoarthritis. Cell Death Dis. 10(7): 522, 2019.

PERROT, S. Osteoarthritis pain. Best practice research Clinical rheumatology, v. 29, n. 1, p. 90-97, 2015.

REIS, C. V.; PORTARO, F. C. V.; ANDRADE, S. A.; FRITZEN, M.; FERNANDES, B.; SAMPAIO, C. A. M.; CAMARGO, A. C. M. & CHUDZINSKI-TAVASSI, A. M. A prothrombin activator serine protease from the *Lonomia obliqua* caterpillar venom (Lopap): biochemical characterization. Thromb. Res. 102: 427-36, 2001a.

REIS, C. V., FARSKY, S. H. P., FERNANDES, B. L., SANTORO, M. L., OLIVA, M. L. V., MARIANO, M., CHUDZINSKI-TAVASSI, A. M. In vivo characterization of Lopap, a prothrombin activator serine protease from the *Lonomia obliqua* caterpillar venom. Thromb. Res. 102:437-43, 2001b.

SPROUSE-BLUM, A. S.; SMITH, G.; SUGAI, D.; PARSA, F. D. Understanding endorphins and their importance in pain management. Hawaii Med J. 69(3): 70-1, 2010.

ZANNIN, M.; LOURENQO, D. M.; MOTTA, G.; DALLA COSTA, L. R.; GRANDO, M.; GAMBORJE, G.; NOGUTI, M. A. & CHUDZINSKI-TAVASSI, A. M. Blood coagulation and fibrinolytic factors in 105 patients with hemorrhagic syndrome caused by accidental contact with *Lonomia obliqua* caterpillar in Santa Catarina, southern Brazil. Thromb. Haemost. 89:355-364, 2003.

ZHOU, P. H.; LIU, S. Q; PENG, H. The effect of hyaluronic acid on IL-1β-induced chondrocyte apoptosis in a rat model of osteoarthritis. Journal of Orthopedic Research. June 3; 26 (12): 1643-1648, 2008.

The invention claimed is:

1. A method of cell remodeling in a subject in need thereof, the method comprising administering a synthetic Cambly peptide comprising the amino acid sequence of SEQ ID NO: 11.

2. The method of claim 1, wherein said cell remodeling comprises reducing inflammation in said subject.

3. The method of claim 2, wherein said cell remodeling comprises treating degenerative disease of an inflammatory nature in said subject.

4. The method of claim 3, wherein said cell degenerative disease comprises rheumatoid arthritis.

5. The method of claim 1, wherein said synthetic Cambly peptide is provided as a pharmaceutical composition, comprising a pharmaceutically acceptable carrier.

* * * * *

```
SEQUENCE LISTING

<160> NUMBER OF SEQ ID NOS: 13

<210> SEQ ID NO 1
```

```
<211> LENGTH: 10
<212> TYPE: PRT
<213> ORGANISM: Artificial Sequence
<220> FEATURE:
<223> OTHER INFORMATION: Designated peptide based on the motif of a
      group of proteins called hemoline from lepidoptera acting as an
      anti-inflammatory molecule.

<400> SEQUENCE: 1

Asp Tyr Trp His Asp Gly His Asp Leu Asn
1               5                   10


<210> SEQ ID NO 2
<211> LENGTH: 10
<212> TYPE: PRT
<213> ORGANISM: Artificial Sequence
<220> FEATURE:
<223> OTHER INFORMATION: Designated peptide based on the motif of a
      group of proteins called hemoline from lepidoptera acting as an
      anti-inflammatory molecule

<400> SEQUENCE: 2

Ile Trp Thr Lys Asp Gly Lys Ala Ile Thr
1               5                   10


<210> SEQ ID NO 3
<211> LENGTH: 10
<212> TYPE: PRT
<213> ORGANISM: Artificial Sequence
<220> FEATURE:
<223> OTHER INFORMATION: Designated peptide based on the motif of a
      group of proteins called hemoline from lepidoptera acting as an
      anti-inflammatory molecule

<400> SEQUENCE: 3

Asn Tyr Phe Lys Asn Gly Lys Asp Val Asn
1               5                   10


<210> SEQ ID NO 4
<211> LENGTH: 10
<212> TYPE: PRT
<213> ORGANISM: Artificial Sequence
<220> FEATURE:
<223> OTHER INFORMATION: Designated peptide based on the motif of a
      group of proteins called hemoline from lepidoptera acting as an
      anti-inflammatory molecule

<400> SEQUENCE: 4

Val Trp Arg Lys Asn Gly Lys Lys Val Ser
1               5                   10


<210> SEQ ID NO 5
<211> LENGTH: 10
<212> TYPE: PRT
<213> ORGANISM: Artificial Sequence
<220> FEATURE:
<223> OTHER INFORMATION: Designated peptide based on the motif of a
      group of proteins called hemoline from lepidoptera acting as an
      anti-inflammatory molecule

<400> SEQUENCE: 5

Thr Trp Asn Lys Lys Gly Lys Lys Val Asn
1               5                   10


<210> SEQ ID NO 6
<211> LENGTH: 10
<212> TYPE: PRT
<213> ORGANISM: Artificial Sequence
<220> FEATURE:
```

```
<223> OTHER INFORMATION: Designated peptide based on the motif of a
      group of proteins called hemoline from lepidoptera acting as an
      anti-inflammatory molecule

<400> SEQUENCE: 6

Ser Trp Leu Lys Asn Gly Arg Glu Phe Arg
1               5                   10


<210> SEQ ID NO 7
<211> LENGTH: 10
<212> TYPE: PRT
<213> ORGANISM: Artificial Sequence
<220> FEATURE:
<223> OTHER INFORMATION: Designated peptide based on the motif of a
      group of proteins called hemoline from lepidoptera acting as an
      anti-inflammatory molecule

<400> SEQUENCE: 7

Gln Pro Glu Ile Ser Trp Thr Arg Asn Lys
1               5                   10


<210> SEQ ID NO 8
<211> LENGTH: 10
<212> TYPE: PRT
<213> ORGANISM: Artificial Sequence
<220> FEATURE:
<223> OTHER INFORMATION: Designated peptide based on the motif of a
      group of proteins called hemoline from lepidoptera acting as an
      anti-inflammatory molecule

<400> SEQUENCE: 8

Arg Trp Leu Lys Asp Gly Gln Ala Phe His
1               5                   10


<210> SEQ ID NO 9
<211> LENGTH: 11
<212> TYPE: PRT
<213> ORGANISM: Artificial Sequence
<220> FEATURE:
<223> OTHER INFORMATION: Designated peptide based on the motif of a
      group of proteins called hemoline from lepidoptera acting as an
      anti-inflammatory molecule

<400> SEQUENCE: 9

Tyr Ala Ile Gly Tyr Ser Cys Lys Asp Tyr Lys
1               5                   10


<210> SEQ ID NO 10
<211> LENGTH: 8
<212> TYPE: PRT
<213> ORGANISM: Artificial Sequence
<220> FEATURE:
<223> OTHER INFORMATION: Designated peptide based on the motif of a
      group of proteins called hemoline from lepidoptera acting as an
      anti-inflammatory molecule

<400> SEQUENCE: 10

Tyr Ser Ile Val Ala Gly Cys Leu
1               5


<210> SEQ ID NO 11
<211> LENGTH: 50
<212> TYPE: PRT
<213> ORGANISM: Artificial Sequence
<220> FEATURE:
<223> OTHER INFORMATION: Designated peptide based on the motif of a
      group of proteins called hemoline from lepidoptera acting as an
      anti-inflammatory molecule
```

-continued

<400> SEQUENCE: 11

Glu Glu Gln Thr His Phe His Phe Glu Ser Pro Lys Leu Ile Ser Phe
1               5                   10                  15

Lys Val Gln Asp Tyr Trp Ile Leu Asn Asp Ile Met Lys Lys Asn Leu
            20                  25                  30

Thr Gly Ile Ser Leu Lys Ser Glu Glu Glu Asp Ala Asp Ser Gly Glu
        35                  40                  45

Ile Asp
    50

<210> SEQ ID NO 12
<211> LENGTH: 62
<212> TYPE: PRT
<213> ORGANISM: Artificial Sequence
<220> FEATURE:
<223> OTHER INFORMATION: Designated peptide based on the motif of a group of proteins called hemoline from lepidoptera acting as an anti-inflammatory molecule

<400> SEQUENCE: 12

Tyr Ser Ile Val Ala Gly Ser Leu Gly Gly Gly Gly Glu Glu Gln Thr
1               5                   10                  15

His Phe His Phe Glu Ser Pro Lys Leu Ile Ser Phe Lys Val Gln Asp
            20                  25                  30

Tyr Trp Ile Leu Asn Asp Ile Met Lys Lys Asn Leu Thr Gly Ile Ser
        35                  40                  45

Leu Lys Ser Glu Glu Glu Asp Ala Asp Ser Gly Glu Ile Asp
    50                  55                  60

<210> SEQ ID NO 13
<211> LENGTH: 65
<212> TYPE: PRT
<213> ORGANISM: Artificial Sequence
<220> FEATURE:
<223> OTHER INFORMATION: Designated peptide based on the motif of a group of proteins called hemoline from lepidoptera acting as an anti-inflammatory molecule

<400> SEQUENCE: 13

Tyr Ala Ile Gly Tyr Ser Ser Lys Asp Tyr Lys Gly Gly Gly Gly Glu
1               5                   10                  15

Glu Gln Thr His Phe His Phe Glu Ser Pro Lys Leu Ile Ser Phe Lys
            20                  25                  30

Val Gln Asp Tyr Trp Ile Leu Asn Asp Ile Met Lys Lys Asn Leu Thr
        35                  40                  45

Gly Ile Ser Leu Lys Ser Glu Glu Glu Asp Ala Asp Ser Gly Glu Ile
    50                  55                  60

Asp
65